(12) United States Patent
Siddiqui et al.

(10) Patent No.: US 8,389,503 B2
(45) Date of Patent: Mar. 5, 2013

(54) STEROIDAL ANTITUBERCULAR COMPOUNDS

(76) Inventors: Bina Siddiqui, Karachi (PK); Nasima Khatoon, Karachi (PK); Sabira Begum, Karachi (PK)

( * ) Notice: Subject to any disclaimer, the term of this patent is extended or adjusted under 35 U.S.C. 154(b) by 139 days.

(21) Appl. No.: 13/037,494

(22) Filed: Mar. 1, 2011

(65) Prior Publication Data

US 2012/0225850 A1  Sep. 6, 2012

(51) Int. Cl.
*A61K 31/56* (2006.01)
(52) U.S. Cl. ........................................ 514/182
(58) Field of Classification Search ............. 514/182
See application file for complete search history.

(56) References Cited

PUBLICATIONS

Ito N, Tamano S, Shirai T. A medium-term rat liver bioassay for rapid in vivo detection of carcinogenic potential of chemicals. Cancer Sci. Jan. 2003;94(1):3-8.*
Siddiqui BS, Khatoon N, Begum S, Sultana R, Durrani SA. Two New Steroids Dehydroandynerizoside and Neristigmol from *Nerium oleander* Leaves. ChemInForm, Jul. 2006; 37(30): U0300.*

* cited by examiner

*Primary Examiner* — Paul Zarek
(74) *Attorney, Agent, or Firm* — Sarfaraz K. Niazi

(57) ABSTRACT

A steroidal compound n-hexyl-p-stigmasteryloxy-benzoate is reported as a novel potent antitubercular drug.

1 Claim, 1 Drawing Sheet

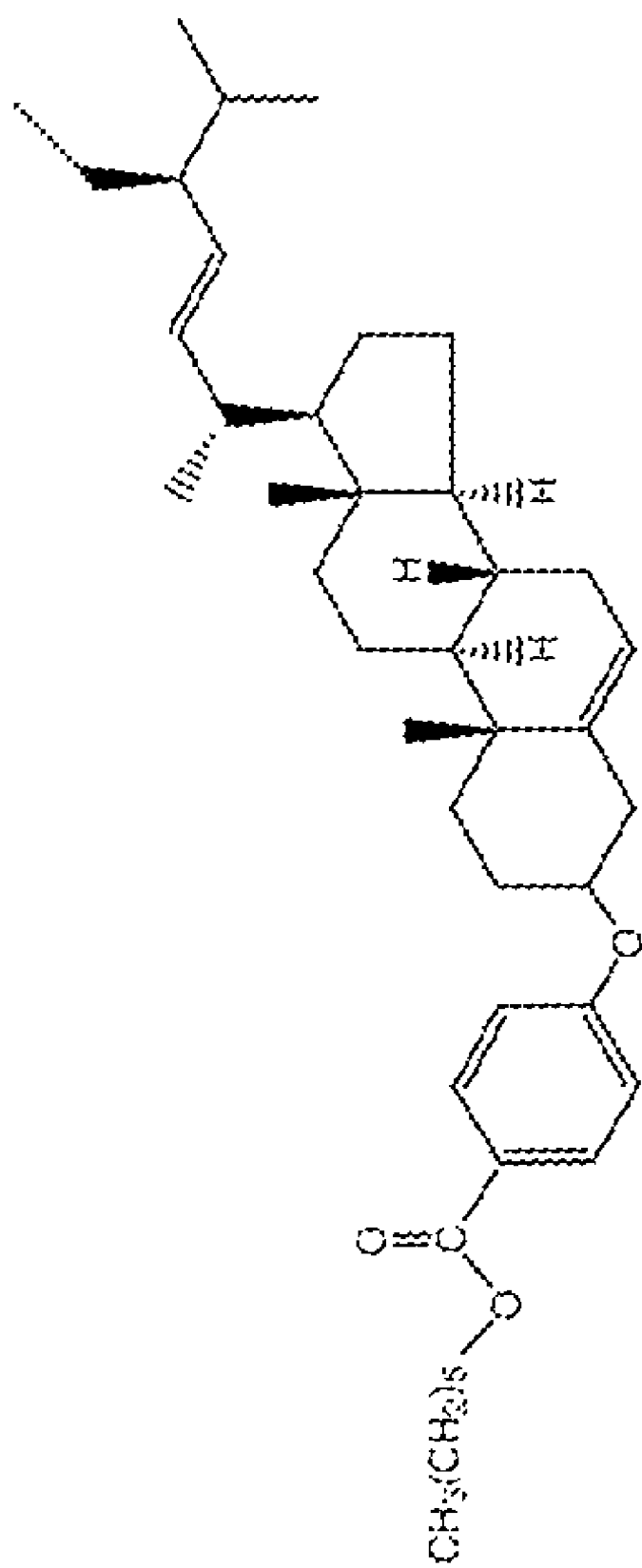

STEROIDAL ANTITUBERCULAR COMPOUNDS

FIELD OF INVENTION

The present invention relates to methods and compositions for treating disease caused by infectious agents, and in particular disease caused by mycobacteria.

BACKGROUND

Tuberculosis (TB) is a contagious disease. Like the common cold, it spreads through the air. Only people who are sick with TB in their lungs are infectious. When infectious people cough, sneeze, talk or spit, they propel TB germs, known as bacilli, into the air. A person needs only to inhale a small number of these to be infected.

Left untreated, each person with active TB disease will infect on average between 10 and 15 people every year. But people infected with TB bacilli will not necessarily become sick with the disease. The immune system "walls off" the TB bacilli which, protected by a thick waxy coat, can lie dormant for years. When someone's immune system is weakened, the chances of becoming sick are greater.

Overall, one-third of the world's population is currently infected with the TB *bacillus*. About 5-10% of people who are infected with TB bacilli (but who are not infected with HIV) become sick or infectious at some time during their life. People with HIV and TB infection are much more likely to develop TB.

WHO estimates that the largest number of new TB cases in 2008 occurred in the South-East Asia Region, which accounted for 35% of incident cases globally. However, the estimated incidence rate in sub-Saharan Africa is nearly twice that of the South-East Asia Region with over 350 cases per 100 000 population.

An estimated 1.7 million people died from TB in 2009. The highest number of deaths was in the Africa Region.

In 2008, the estimated per capita TB incidence was stable or falling in all six WHO regions. However, the slow decline in incidence rates per capita is offset by population growth. Consequently, the number of new cases arising each year is still increasing globally in the WHO regions of Africa, the Eastern Mediterranean and South-East Asia.

The new reports on the incidence, prevalence and mortality from tuberculosis are alarming (Global tuberculosis control 2010, WHO). Accordingly, the prevalence of TB is the lowest in The Americas at 37/100,000 while corresponding prevalence is 63 in Europe, 160 in Western Pacific, 280 in South-East Asia and 450 in Africa. The mortality rates are accordingly, 2.1 in The Americas to 50 in Africa. Africa accounts for almost 30% of all new cases of tuberculosis, The Americas only 2.9% and the highest incidence is found in South-East-Asia which accounts for 35% of new cases.

HIV and TB form a lethal combination, each speeding the other's progress. HIV weakens the immune system. Someone who is HIV-positive and infected with TB bacilli is many times more likely to become sick with TB than someone infected with TB bacilli who is HIV-negative. TB is a leading cause of death among people who are HIV-positive. In Africa, HIV is the single most important factor contributing to the increase in the incidence of TB since 1990.

WHO and its international partners have formed the TB/HIV Working Group, which develops global policy on the control of HIV-related TB and advises on how those fighting against TB and HIV can work together to tackle this lethal combination. The interim policy on collaborative TB/HIV activities describes steps to create mechanisms of collaboration between TB and HIV/AIDS programs, to reduce the burden of TB among people and reducing the burden of HIV among TB patients.

Until 50 years ago, there were no medicines to cure TB. Now, strains that are resistant to a single drug have been documented in every country surveyed; what is more, strains of TB resistant to all major anti-TB drugs have emerged. Drug-resistant TB is caused by inconsistent or partial treatment, when patients do not take all their medicines regularly for the required period because they start to feel better, because doctors and health workers prescribe the wrong treatment regimens, or because the drug supply is unreliable. A particularly dangerous form of drug-resistant TB is multi-drug-resistant TB (MDR-TB), which is defined as the disease caused by TB bacilli resistant to at least isoniazid and rifampicin, the two most powerful anti-TB drugs. Rates of MDR-TB are high in some countries, especially in the former Soviet Union, and threaten TB control efforts.

While drug-resistant TB is generally treatable, it requires extensive chemotherapy (up to two years of treatment) with second-line anti-TB drugs which are more costly than first-line drugs, and which produce adverse drug reactions that are more severe, though manageable. Quality assured second-line anti-TB drugs are available at reduced prices for projects approved by the Green Light Committee.

The emergence of extensively drug-resistant (XDR) TB, particularly in settings where many TB patients are also infected with HIV, poses a serious threat to TB control, and confirms the urgent need to strengthen basic TB control and to apply the new WHO guidelines for the programmatic management of drug-resistant TB.

Although over 37 species of mycobacteria have been identified, more than 95% of all human infections are caused by six species of mycobacteria: *M. tuberculosis, M. avium* intracellulare, *M. kansasii, M. fortuitum, M. chelonae,* and *M. leprae*. The most prevalent mycobacterial disease in humans is tuberculosis (TB), which is predominantly caused by mycobacterial species comprising *M. tuberculosis, M. bovis,* or *M. africanum* (Merck Manual 1992). Infection is typically initiated by the inhalation of infectious particles, which are able to reach the terminal pathways in lungs. Following engulfment by alveolar macrophages, the bacilli are able to replicate freely, with eventual destruction of the phagocytic cells. A cascade effect ensues wherein destruction of the phagocytic cells causes additional macrophages and lymphocytes to migrate to the site of infection, where they too are ultimately eliminated. The disease is further disseminated during the initial stages by the infected macrophages which travel to local lymph nodes, as well as into the blood stream and other tissues such as the bone marrow, spleen, kidneys, bone and central nervous system. (See Murray et al. Medical Microbiology, The C.V. Mosby Company 219-230 (1990)).

There is still no clear understanding of the factors which contribute to the virulence of mycobacteria. Many investigators have implicated lipids of the cell wall and bacterial surface as contributors to colony morphology and virulence. Evidence suggests that C-mycosides, on the surface of certain mycobacterial cells, are important in facilitating survival of the organism within macrophages. Trehalose 6,6' dimycolate, a cord factor, has been implicated for other mycobacteria.

The interrelationship of colony morphology and virulence is particularly pronounced in *M. avium. M. avium* bacilli occur in several distinct colony forms. Bacilli, which grow, as transparent, or rough, colonies on conventional laboratory media are multiplicable within macrophages in tissue culture, are virulent when injected into susceptible mice, and are resistant to antibiotics. Rough or transparent bacilli, which are maintained on laboratory culture media, often spontaneously assume an opaque R colony morphology, at which time they are not multiplicable in macrophages, are avirulent in mice, and are highly susceptible to antibiotics. The differences in colony morphology between the transparent, rough and opaque strains of *M. avium* are almost certainly due to the presence of a glycolipid coating on the surface of transparent and rough organisms, which acts as a protective capsule. This capsule, or coating, is composed primarily of C-mycosides which apparently shield the virulent *M. avium* organisms from lysosomal enzymes and antibiotics. By contrast, the non-virulent opaque forms of *M. avium* have very little C-mycoside on their surface. Both the resistance to antibiotics and the resistance to killing by macrophages have been attributed to the glycolipid barrier on the surface of *M. avium.*

Diagnosis of mycobacterial infection is confirmed by the isolation and identification of the pathogen, although conventional diagnosis is based on sputum smears, chest X-ray examination (CXR), and clinical symptoms. Isolation of mycobacteria on a medium takes as long as four to eight weeks. Species identification takes a further two weeks. There are several other techniques for detecting mycobacteria such as the polymerase chain reaction (PCR), *mycobacterium tuberculosis* direct test, or amplified *mycobacterium tuberculosis* direct test (MTD), and detection assays that utilize radioactive labels.

One diagnostic test that is widely used for detecting infections caused by *M. tuberculosis* is the tuberculin skin test. Although numerous versions of the skin test are available, typically one of two preparations of tuberculin antigens are used: old tuberculin (OT), or purified protein derivative (PPD). The antigen preparation is either injected into the skin intradermally, or is topically applied and is then invasively transported into the skin with the use of a multi-prong inoculator (Tine test). Several problems exist with the skin test diagnosis method. For example, the Tine test is not generally recommended because the amount of antigen injected into the intradermal layer cannot be accurately controlled. (See Murray et al. Medical Microbiology, The C.V. Mosby Company 219-230 (1990)). Although the tuberculin skin tests are widely used, they typically require two to three days to generate results, and many times, the results are inaccurate since false positives are sometimes seen in subjects who have been exposed to mycobacteria, but are healthy. In addition, instances of misdiagnosis are frequent since a positive result is observed not only in active TB patients, but also in persons vaccinated with Bacille Calmette-Guerin (BCG), and those who had been infected with mycobacteria, but have not developed the disease. It is hard therefore, to distinguish active TB patients from the others, such as household TB contacts, by the tuberculin skin test. Additionally, the tuberculin test often produces a cross-reaction in those individuals who were infected with mycobacteria other than *M. tuberculosis* (MOTT). Therefore, diagnosis using the skin tests currently available is frequently subject to error and inaccuracies.

The standard treatment for tuberculosis caused by drug-sensitive organisms is a six-month regimen consisting of four drugs given for two months, followed by two drugs given for four months. The two most important drugs, given throughout the six-month course of therapy, are isoniazid and rifampin. Although the regimen is relatively simple, its administration is quite complicated. Daily ingestion of eight or nine pills is often required during the first phase of therapy; a daunting and confusing prospect. Even severely ill patients are often symptom free within a few weeks, and nearly all appear to be cured within a few months. If the treatment is not continued to completion, however, the patient may experience a relapse, and the relapse rate for patients who do not continue treatment to completion is high. A variety of forms of patient-centered care are used to promote adherence with therapy. The most effective way of ensuring that patients are taking their medication is to use directly observed therapy, which involves having a member of the health care team observe the patient take each dose of each drug. Directly observed therapy can be provided in the clinic, the patient's residence, or any mutually agreed upon site. Nearly all patients who have tuberculosis caused by drug-sensitive organisms, and who complete therapy will be cured, and the risk of relapse is very low ("Ending Neglect: The Elimination of Tuberculosis in the United States" ed. L. Geiter Committee on the Elimination of Tuberculosis in the United States Division of Health Promotion and Disease Prevention, Institute of Medicine. 2000.)

Needed are effective therapeutic regimens that include improved vaccination and treatment protocols. Currently available therapeutics are no longer consistently effective as a result of the problems with treatment compliance, and these compliance problems contribute to the development of drug resistant mycobacterial strains.

Clearly effective therapeutic regimens that include improved vaccination and treatment protocols are needed. A therapeutic vaccine that would prevent the onset of tuberculosis, and therefore eliminate the need for therapy is desirable. Although currently available therapeutic measures are effective, the emergence of drug resistant strains has necessitated new formulations and compositions that are more versatile than current drugs. What is needed are new anti-tubercular drugs that provide highly effective treatment, and shorten and simplify tuberculosis chemotherapy.

SUMMARY OF INVENTION

BRIEF DESCRIPTION OF DRAWING

FIG. 1. Stereochemical structure of Compound I, which is n-hexyl-p-stigmasteryloxy-benzoate.

The present invention also relates to methods and compositions having improved anti-mycobacterial activity, namely compositions comprising a novel antitubercular steroid.

The present invention relates to a novel use of a steroid analog, their preparation, and their use as pharmaceuticals and pharmaceutical compositions containing them.

More particularly the invention provides a new use of compound of formula n-hexyl-p-stigmasteryloxy-benzoate. (Compound I).

Compound I

FIG. 1

On account of the asymmetrical carbon atom(s) which is (are) present in Compound I, the compound may appear in optically active form or in form of mixtures of optical isomers, e.g., in form of racemic mixtures. All optical isomers and their mixtures including the racemic mixtures are part of the present invention.

Compound I exhibits valuable pharmacological properties when tested in vitro using tuberculosis agent, and in level I and level II assay of toxicity using mammalian VERO cells lines, and are therefore useful as pharmaceuticals.

In particular the agent of the invention shows high activity against tuberculosis organism. The agent of the invention is therefore useful for treatment of tuberculosis.

Accordingly in a further aspect the present invention provides the agents of the invention for use as pharmaceuticals, more specifically for treatment in the above-mentioned conditions, e.g., tuberculosis.

The present invention furthermore provides a pharmaceutical composition comprising an agent of the invention in association with at least one pharmaceutically acceptable diluent or carrier. Such compositions may be formulated in conventional manner.

Agents of the invention may be administered by any conventional route, for example parenterally e.g. in form of injectable solutions or suspensions, or enterally, preferably orally, e.g., in the form of tablets or capsules.

The agents of the invention may alternatively be administered e.g. topically in the form of a cream, gel or the like, or by inhalation, e.g., in dry powder form.

Examples for compositions comprising an agent of the invention include, e.g., a solid dispersion, an aqueous solution, e.g. containing a solubilizing agent, a microemulsion and a suspension of an agent of the invention. The composition may be buffered to a pH in the range of e.g., from 3.5 to 9.5, by a suitable buffer.

The agents of the invention can be administered either alone or in combination with other pharmaceutical agents effective in the treatment of conditions mentioned above.

Thus, the agents of the invention can be used for the treatment of tuberculosis in combination with: ethambutol, isoniazid, pyrazinamide, rifampicin, streptomycin, ciprofloxacin, norfloxacin and p-aminosalicylic acid.

The pharmaceutical compositions for separate administration of the combination partners and for the administration in a fixed combination, i.e., a single galenical composition comprising at least two combination partners according to the invention, can be prepared in a manner known per se and are thus suitable for enteral, such as oral or rectal, and parenteral administration to mammals, including man, comprising a therapeutically effective amount of at least one pharmacologically active combination partner alone or in combination with one or more pharmaceutically acceptable carriers, especially suitable for enteral or parenteral application.

In particular, a therapeutically effective amount of each of the combination partners may be administered simultaneously or sequentially and in any order, and the components may be administered separately or as fixed combination.

Accordingly the invention also provides a combination comprising a therapeutically effective amount of an agent of the invention and a second drug substance, said second drug substance being for example for use in any of the particular indications herein before set forth.

The preferred indications are treatment of tuberculosis.

The preferred agent of the invention for the above-mentioned indications is n-hexyl-p-stigmasteryloxy-benzoate.

In accordance with the foregoing, the present invention also provides the use of an agent of the invention as a pharmaceutical, e.g., for the treatment of tuberculosis.

Moreover the present invention provides the use of an agent of the invention for the manufacture of a medicament for the treatment of any condition mentioned above, e.g., tuberculosis.

The following examples illustrate the invention.

EXAMPLE 1

Method for Preparation of n-hexyl-p-stigmasteryloxy-benzoate (neristigmol)

Fresh and uncrushed Nerium oleander leaves (40 kg) were extracted with MeOH at room temperature. The concentrated syrupy residue obtained on removal of the solvent was shaken out with EtOAc and $H_2O$. The EtOAc layer was extracted with 4% aqueous $Na_2CO_3$ solution to separate the acidic fraction from the neutral fraction. The EtOAc layer containing the neutral fraction was washed, dried over anhydrous $Na_2SO_4$, charcoaled and concentrated to a syrupy mass. It was divided into n-hexane soluble (N-HS) and insoluble (N-HI) fractions. The fraction N-HS was partitioned between 90% aq. MeOH and hexane. The aqueous methanol phase obtained was extracted out with EtOAc after saturation with saline. The EtOAc phase was dried over anhydrous $Na_2SO_4$ and vacuum dried. The residue obtained was again treated with n-hexane to obtain n-hexane insoluble (N-HS-MP-HI) and n-hexane soluble (N-HS-MP-HS) fractions. Fraction (N-HS-MP-HI) (9.7 g) was treated with EtOAc to obtain EtOAc insoluble and EtOAc soluble fractions. On concentrating the EtOAc soluble fraction to about 50% volume an insoluble residue settled down which was filtered off. The filtrate was reduced in volume and poured in excess of hexane when an insoluble mass separated out which was removed by filtration. The filtrate was vacuum dried to yield a cream colored residue (2.5 g). This residue was dissolved in a small quantity of chloroform and kept over night at room temperature when a white amorphous solid separated out which was filtered, recrystallized from MeOH and characterized as stigmasterol (500 mg). The mother liquor was subjected to classical column chromatography using gradient mixtures of 0-100% EtOAc in hexane, then 0-30% MeOH in $CHCl_3$, resulting in eleven pooled fractions. Fraction No. 10 (900 mg) was again separated on classical column of silica gel using gradient mixtures of 0-100% EtOAc in hexane, then 0-30% MeOH in $CHCl_3$, resulting in four pooled fractions. Fraction No. 3 (68 mg) was further purified on aluminium cards pre-coated with silica gel (hexane-EtOAc; 7:3) into two bands. The faster moving band consisted of a mixture of known sterols while the polar band was characterized as a new sterol, neristigmol (18.2 mg). [Siddiqui, B.; Khatoon, N.; Begum, S.; Sultana, R.; Durrani, S., Two New Steroids Dehydroadynerizoside and Neristigmol from Nerium oleander Leaves. Polish Journal of Chemistry, 2006, Vol. 80, nr 3, s. 445-452.]

DETAILED DESCRIPTION

The present invention comprises methods and compositions comprising a novel use of Compound I for the treatment of infectious disease. The compositions of the present invention have improved anti-mycobacterial activity, and more particularly, improved anti-tuberculosis activity.

The present invention may be understood more readily by reference to the following detailed description of the specific embodiments included herein. However, although the present invention has been described with reference to specific details of certain embodiments thereof, it is not intended that such details should be regarded as limitations upon the scope of the invention.

Mycobacterial infections, such as those causing tuberculosis, once thought to be declining in occurrence, have rebounded, and again constitute a serious health threat. Tuberculosis (TB) is the cause of the largest number of human deaths attributed to a single etiologic agent with two to three million people infected with tuberculosis dying each year. Areas where humans are crowded together, or living in substandard housing, are increasingly found to have persons affected with mycobacteria. Individuals who are immunocompromised are at great risk of being infected with mycobacteria and dying from such infection. In addition, the emergence of drug-resistant strains of mycobacteria has led to treatment problems of such infected persons.

Many people who are infected with mycobacteria are poor, or live in areas with inadequate healthcare facilities. As a result of various obstacles (economical, education levels, etc.), many of these individuals are unable to comply with prescribed therapeutic regimens. Ultimately, persistent noncompliance by these and other individuals results in the prevalence of disease. This noncompliance is frequently compounded by the emergence of drug-resistant strains of mycobacteria. Effective compositions and vaccines that target various strains of mycobacteria are necessary to bring the increasing number of tuberculosis cases under control.

Chemotherapy is a standard treatment for tuberculosis. Some current chemotherapy treatments require the use of three or four drugs, in combination, administered daily for two months, or administered biweekly for four to twelve months. Decades of misuse of existing antibiotics and poor compliance with prolong and complex therapeutic regimens has led to mutations of the *mycobacterium tuberculosis* and has created an epidemic of drug resistance that threatens tuberculosis control worldwide. The vast majority of currently prescribed drugs, including the front line drugs, such as isoniazid, rifampin, pyrazinamide, ethambutol and streptomycin were developed from the 1950s to the 1970s. Thus, this earlier development of tuberculosis chemotherapy did not have at its disposal the implications of the genome sequence of *Mycobacterium tuberculosis*, the revolution in pharmaceutical drug discovery of the last decades, and the use of rational drug testing and combinational chemistry.

Consequently, the treatments of drug-resistant *M. tuberculosis* strains, and latent tuberculosis infections, require new anti-tuberculosis drugs that provide highly effective treatments, and shortened and simplified tuberculosis chemotherapies. Moreover, it is desirable that these drugs be prepared by a low-cost synthesis, since the demographics of the disease dictate that cost is a significant factor.

The present invention provides methods and compositions comprising a novel application of steroids compounds effective in treatment and prevention of disease caused by microorganisms including, but not limited to, bacteria. In particular, the methods and compositions of the present invention are effective in inhibiting the growth of the microorganism, *M. tuberculosis*. The methods and compositions of the present invention are intended for the treatment of mycobacteria infections in human, as well as other animals. For example, the present invention may be particularly useful for the treatment of cows infected by *M. bovis.*

As used herein, the term "tuberculosis" comprises disease states usually associated with infections caused by mycobacteria species such as those comprising *M. tuberculosis* complex. The term "tuberculosis" is also associated with mycobacterial infections caused by mycobacteria other than *M. tuberculosis* (MOTT). Other mycobacterial species include, but are not limited to, *M. avium-intracellulare, M. kansarii, M. fortuitum, M. chelonae, M. leprae, M. africanum*, and *M. microti, M. avium paratuberculosis, M. intracellulare, M. scrofulaceum, M. xenopi, M. marinum, M. ulcerans.*

The present invention further comprises methods and compositions effective for the treatment of infectious disease including, but not limited to, those caused by bacterial, mycological, parasitic, and viral agents. Examples of such infectious agents include the following: *staphylococcus*, streptococcaceae, neisseriaceae, cocci, enterobacteriaceae, pseudomonadaceae, vibrionaceae, *campylobacter*, pasteurellaceae, *bordetella, francisella, brucella*, legionellaceae, bacteroidaceae, gram-negative bacilli, *clostridium, corynebacterium, propionibacterium*, gram-positive bacilli, anthrax, *actinomyces, nocardia, mycobacterium, treponema, borrelia, leptospira, mycoplasma, ureaplasma, rickettsia*, chlamydiae, systemic mycoses, opportunistic mycoses, protozoa, nematodes, trematodes, cestodes, adenoviruses, herpesviruses, poxviruses, papovaviruses, hepatitis viruses, orthomyxoviruses, paramyxoviruses, coronaviruses, picornaviruses, reoviruses, togaviruses, flaviviruses, bunyaviridae, rhabdoviruses, human immunodeficiency virus and retroviruses.

The present invention further provides methods and compositions useful for the treatment of infectious disease, including but not limited to, tuberculosis, leprosy, Crohn's Disease, acquired immunodeficiency syndrome, lyme disease, cat-scratch disease, Rocky Mountain Spotted Fever and influenza.

Details for Characterization of n-hexyl-p-stigmasteryloxybenzoate (neristigmol)

Full chemical formula: $C_{42}H_{64}O_3$

Details of Spectral Data Used to Identify Compound I:

UV $\lambda_{max}$ (MeOH) nm 252

IR $\nu_{max}$. ($CHCl_3$) $cm^{-1}$ 2932.3, 2869.3 (CH stretching), 1709.3 (C═O), 1609.1-1458.2 (aromatic CH)

FAB-MS m/z 616 [$M^+$]

HR-EIMS m/z (rel. int. %) 412.7032 ($C_{29}H_{48}O$, $M^+$-hexylbenzoic acid-H) (40.7), (calcd. for $C_{29}H_{48}O$, 412.7053); 396.6998 ($C_{29}H_{48}$) (17.9), 273.4410 ($C_{19}H_{29}O$) (14.5), 255.4237 ($C_{19}H_{27}$) (17.5), 121.1070 ($C_7H_5O_2$) (26.6), 105.1121 ($C_7H_5O$) (28.8), 84.1609 ($C_6H_{12}$) (29.8), 55.0774 ($C_4H_7$) (100).

$^1H$- and $^{13}C$-NMR data Table-1

TABLE 1

$^1H$ and $^{13}C$ NMR spectral data of N-III-10-2 in $CDCl_3$ (d in ppm, J in Hz).

| H/C | $\delta_H$ | $\delta_C$ |
|---|---|---|
| 1 | 1.09 m | 37.24 |
| 2 | 2a, 1.79 m<br>2b, 1.80 m | 31.6 |
| 3 | 3.52 dddd (11.1, 5.2) | 79.0 |
| 4 | 2.25 m | 42.2 |
| 5 | — | 140.7 |
| 6 | 5.20 br.s | 121.7 |
| 7 | 1.95 m | 32.0 |
| 8 | 1.84 m | 36.1 |
| 9 | 1.53 m | 51.2 |
| 10 | | 37.0 |
| 11 | 1.51 | 21.07 |
| 12 | 1.90 m | 39.7 |
| 13 | — | 41.2 |
| 14 | 1.20 m | 56.8 |
| 15 | 1.23 br.s | 24.3 |
| 16 | 1.10 m | 26.1 |
| 17 | 0.70 m | 55.9 |
| 18 | 1.09 s | 19.3 |
| 19 | 0.77 s | 12.0 |
| 20 | 2.02 m | 40.4 |
| 21 | 0.91 d (6.5) | 18.9 |
| 22 | 5.17 dd (15.7, 8.5) | 138.3 |
| 23 | 5.01 dd (15.7, 8.5) | 129.2 |
| 24 | 1.93 m | 50.1 |
| 25 | 1.40 m | 28.1 |
| 26 | 0.83 d (6.5) | 21.2 |
| 27 | 0.81 d (6.5) | 20.6 |
| 28 | 1.23 m | 23.3 |
| 29 | 0.82 t (6.2) | 12.2 |
| 1' | — | 160.1 |
| 2' | 6.82 d (8.7) | 115.1 |
| 3' | 7.90 d (8.7) | 131.8 |
| 4' | — | 125.5 |
| 5' | 7.90 d (8.7) | 131.8 |
| 6' | 6.82 d (8.7) | 115.1 |
| 7' | — | 165.1 |
| 1" | 4.22 t (6.6) | 66.2 |
| 2" | 1.28 m | 31.6 |
| 3" | 1.28 m | 24.2 |
| 4" | 1.28 m | 23.0 |

TABLE 1-continued $^1$H and $^{13}$C NMR spectral data of N-III-10-2 in CDCl$_3$ (d in ppm, J in Hz).

| H/C | $\delta_H$ | $\delta_C$ |
|---|---|---|
| 5" | 1.19 m | 22.0 |
| 6" | 0.81 (7.5) | 15.6 |

The assignments are based on $^1$H-$^1$H COSY, J-resolved and HMQC spectra data.

FORMULATIONS

Therapeutics, including compositions containing Compound I of the present invention, can be prepared in physiologically acceptable formulations, such as in pharmaceutically acceptable carriers, using known techniques. The compositions of the present invention may be administered in the form of a solid, liquid or aerosol. Examples of solid compositions include pills, creams, soaps and implantable dosage units. Pills may be administered orally. Therapeutic creams and anti-mycobacteria soaps may be administered topically. Implantable dosage units may be administered locally, for example, in the lungs, or may be implanted for systematic release of the therapeutic composition, for example, subcutaneously. Examples of liquid compositions include formulations adapted for injection intramuscularly, subcutaneously, intravenously, intraarterially, and formulations for topical and intraocular administration. Examples of aerosol formulations include inhaler formulations for administration to the lungs.

A sustained release matrix, as used herein, is a matrix made of materials, usually polymers, which are degradable by enzymatic or acid/base hydrolysis, or by dissolution. Once inserted into the body, the matrix is acted upon by enzymes and body fluids. The sustained release matrix is chosen desirably from biocompatible materials, including, but not limited to, liposomes, polylactides, polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipds, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide.

The dosage of the composition will depend on the condition being treated, the particular composition used, and other clinical factors, such as weight and condition of the patient, and the route of administration.

The composition may be administered in combination with other compositions and procedures for the treatment of other disorders occurring in combination with mycobacterial disease. For example, tuberculosis frequently occurs as a secondary complication associated with acquired immunodeficiency syndrome (AIDS). Patients undergoing AIDS treatment, which includes procedures such as surgery, radiation or chemotherapy, may benefit from the therapeutic methods and compositions described herein.

In Vitro Efficacy Studies

Primary Screen (Dose Response): Determination of a 90% Inhibitory Concentration (IC90). The initial screen is conducted against *Mycobacterium tuberculosis* H37Rv (ATCC 27294) in BACTEC 12B medium using the Microplate Alamar Blue Assay (MABA). Compounds are tested in ten 2-fold dilutions, typically from 100 µg/mL to 0.19 µg/mL. The IC90 is defined as the concentration effecting a reduction in fluorescence of 90% relative to controls. This value is determined from the dose-response curve using a curve-fitting program. Any IC90 value of $\leq$10 µg/mL is considered "Active" for antitubercular activity. Its Level-I assays of antituberculosis activity indicated excellent IC90 (6.25 µg/mL), therefore it was subjected to Level-II assays Secondary Screen: Determination of Mammalian Cell Cytotoxicity (CC50). The VERO cell cytotoxicity assay is done in parallel with the TB Dose Response assay. After 72 hours exposure, viability is assessed using Promega's Cell Titer Glo Luminescent Cell Viability Assay, a homogeneous method of determining the number of viable cells in culture based on quantitation of the ATP present. Cytotoxicity is determined from the dose-response curve as the CC50 using a curve-fitting program. The CC50 was 79.59 ug/mL. Ultimately, the CC50 is divided by the IC90 to calculate an SI (Selectivity Index) value. SI values of $\geq$10 are considered for further testing. The Selectivity Index (SI) was found to be 12.73, which suggests that it is highly effective antituberculosis agent. (Collins, L. A. and Franzblau, S. G. 1997. Microplate Alamar Blue Assay versus BACTEC 460 System for High-Throughput Screening of Compounds against *Mycobacterium tuberculosis* and *Mycobacterium avium*. Antimicrob. Agents.)

What is claimed is:

1. A method for the treatment of tuberculosis in a subject in need of such treatment, which comprises administering to such subject a therapeutically effective amount of n-hexyl-p-stigmasteryloxy-benzoate (neristigmol).

* * * * *